(12) United States Patent
DeCarlo et al.

(10) Patent No.: US 6,409,748 B1
(45) Date of Patent: Jun. 25, 2002

(54) HEATING PAD WITH REMOVABLE GEL PACK

(75) Inventors: Arnold V. DeCarlo, Manhattan; Robert Czajkowski, Tinley Park, both of IL (US)

(73) Assignee: Sunbeam Products, Inc., Boca Raton, FL (US)

( * ) Notice: Subject to any disclaimer, the term of this patent is extended or adjusted under 35 U.S.C. 154(b) by 0 days.

(21) Appl. No.: 09/441,282

(22) Filed: Nov. 16, 1999

(51) Int. Cl.[7] .................................................. A61F 7/00
(52) U.S. Cl. ........................... 607/114; 607/98; 607/96; 607/112
(58) Field of Search ............................ 607/98, 114, 96, 607/112

(56) References Cited

U.S. PATENT DOCUMENTS

| | | | | |
|---|---|---|---|---|
| 4,846,176 A | * | 7/1989 | Golden | 128/400 |
| 5,007,416 A | * | 4/1991 | Burns et al. | 128/80 |
| 5,050,595 A | * | 9/1991 | Krafft | 128/379 |
| 5,062,414 A | * | 11/1991 | Grim | 128/68 |
| 5,335,255 A | * | 8/1994 | Kanare et al. | 607/149 |
| 5,800,490 A | * | 9/1998 | Patz et al. | 607/108 |
| 5,835,983 A | * | 11/1998 | McMahen et al. | 219/527 |
| 6,165,208 A | * | 12/2000 | Reyes et al. | 607/112 |

OTHER PUBLICATIONS

Product Sell Sheet For Cold Pack—Model 1751-8—(1999).
Product Sell Sheet For Heat To Go—Large Heat Wrap—Model 1763-8—(1999).
Product Sell Sheet For Heat To Go—Medium Heat Wrap—Model 1762-8—(1999).
Product Sell Sheet For Heat To Go—Heat Wrap—Model 1761-8—(1999).
Product Sell Sheet For Heat To Go—Small Heat Wrap—Model 1760-8—(1999).

* cited by examiner

Primary Examiner—Michael Peffley
Assistant Examiner—Jocelyn Ram
(74) Attorney, Agent, or Firm—Kramer, Levin, Naftalis & Frankel LLP

(57) ABSTRACT

The present invention provides a heating pad capable of rapid initial heat transfer to a heating pad member by means of a removable gel pack member which is releasably attached to the heating pad member. The heating pads of the present invention are useful for the rapid and convenient treatment of various muscular and orthopedic aches and pains.

33 Claims, 6 Drawing Sheets

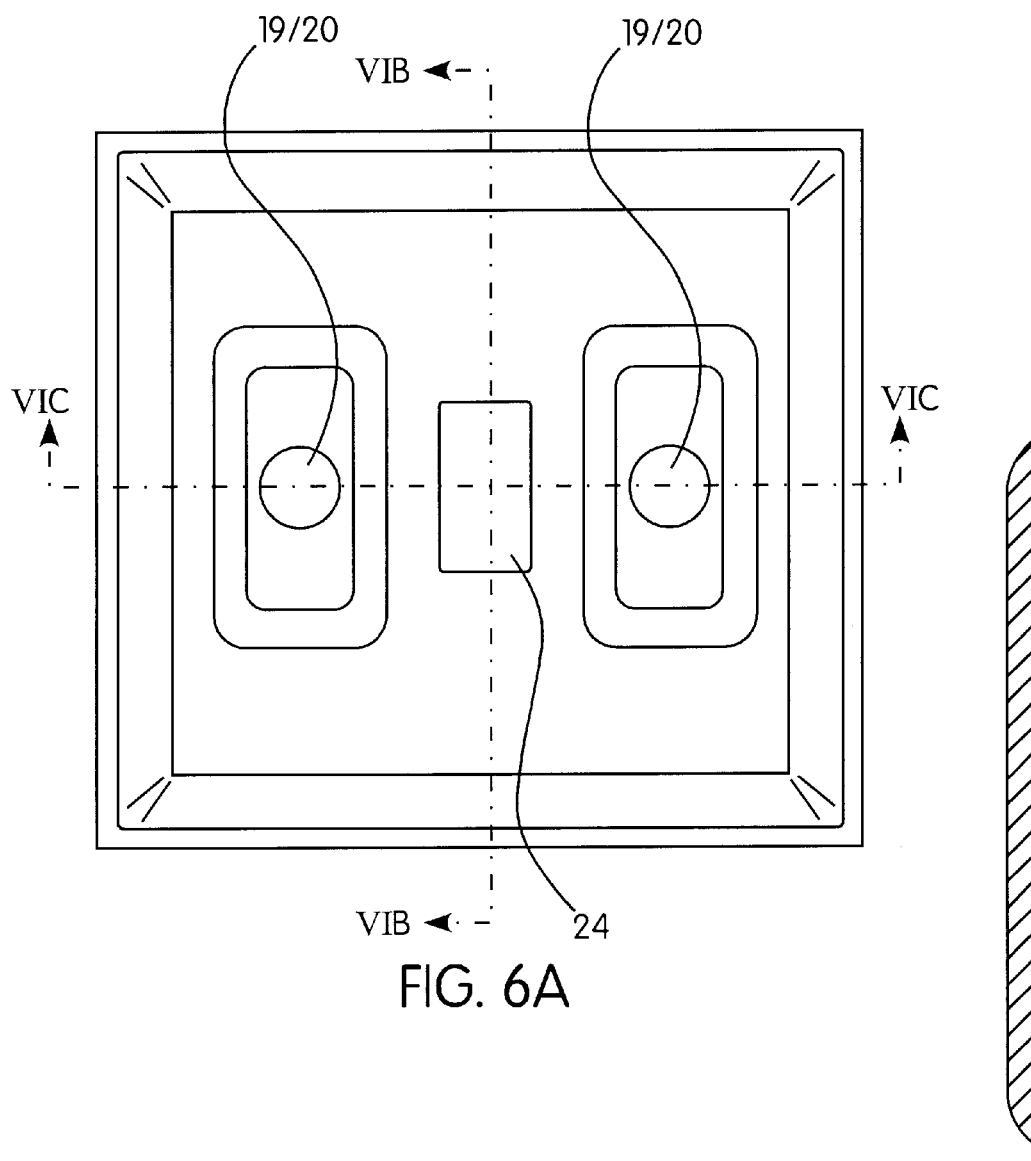
FIG. 6A
FIG. 6B
FIG. 6C

HEATING PAD WITH REMOVABLE GEL PACK

BACKGROUND OF THE INVENTION

The present invention relates generally to improvements in heating pads and particularly to heating pads having removable gel packs which provide a rapid warming capability.

The value of heat treatment for easing and preventing the onset of pain in muscle tissues is well established. For example, muscles which tend to cramp may be heated before strenuous exercise to enrich the blood supply to the appropriate areas. Means for effecting such heat treatment include the use of electrical heating pads. However, conventional heating pads used in treating patients in need of heat therapy suffer from several inconveniences. Slow heat-up times result from increased padding which is often used to improve comfort by providing more even heat distribution. Speeding heat-up by increasing electrical current or reducing the padding filler typically causes uncomfortable and potentially dangerous localized hot spots. An enhanced design which permits rapid initial transfer of heat to a subject prior to the time regular $I^2R$ heating can achieve a similar heat transfer would avoid the delay in providing treatment using standard heating pads.

SUMMARY OF THE INVENTION

Accordingly, it is an object of the present invention to provide an improved heating pad comprising a heating pad member and a removable gel pack which can be rapidly heated to a desired temperature prior to attachment to a heating pad member.

Another object of the present invention is to provide a heating pad which is capable of rapid heating with increased comfort using standard wattage and padding thicknesses.

Accordingly, the present invention provides a heating pad for a subject in need of heat therapy comprising a heating pad member comprising a cover and electrical heating coils, wherein the cover comprises an inner layer and an outer layer, and a removable gel pack member which contacts an anatomical portion of the subject and is releasably attached to the inner layer, wherein each layer comprises a flexible fabric material and has a plurality of sides which are permanently secured together, and wherein the removable gel pack member comprises a heat-retentive gel. The electrical heating coils are enclosed by the cover and are substantially evenly distributed within the cover. The present invention conveniently permits preliminary heating of the gel pack member to a predetermined temperature prior to attachment to the inner layer, and additionally permits the maintenance of the predetermined temperature during application of the heating pad to the subject by operating the electrical heating coils.

The accompanying drawings, referred to herein and constituting a part hereof, illustrate preferred embodiments of the present invention and, together with the description, serve to explain the principles of the present invention.

BRIEF DESCRIPTION OF THE DRAWINGS

FIGS. 6A, 6B and 6C are top diagrammatic and side cross-sectional views with detail of a removable gel pack in accordance with the present invention.

Figure 1:
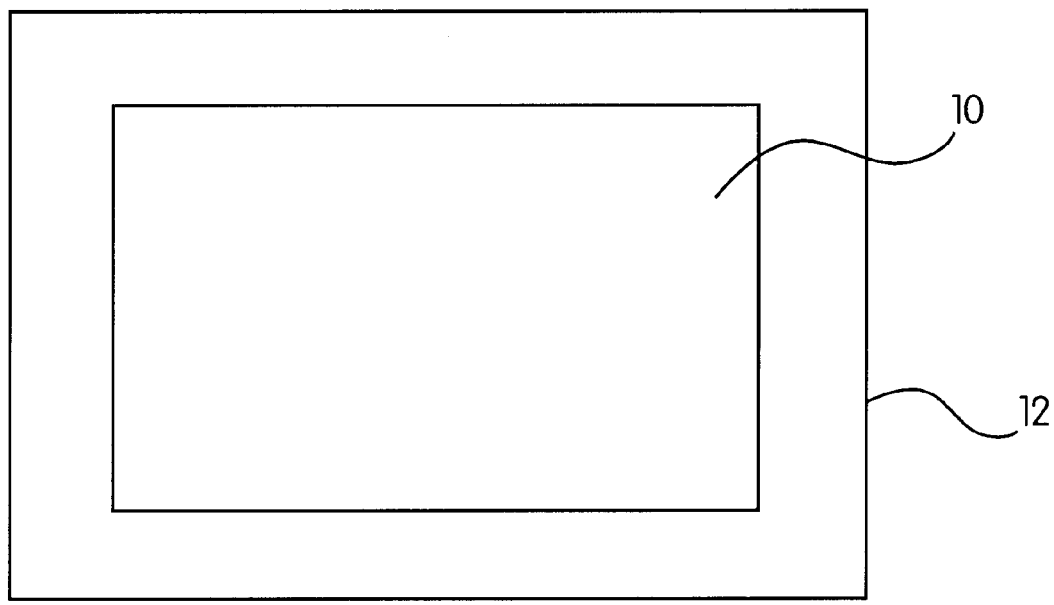
FIG. 1 is a perspective view of an embodiment of a heating pad with removable gel pack in accordance with the present invention.
Figure 2:
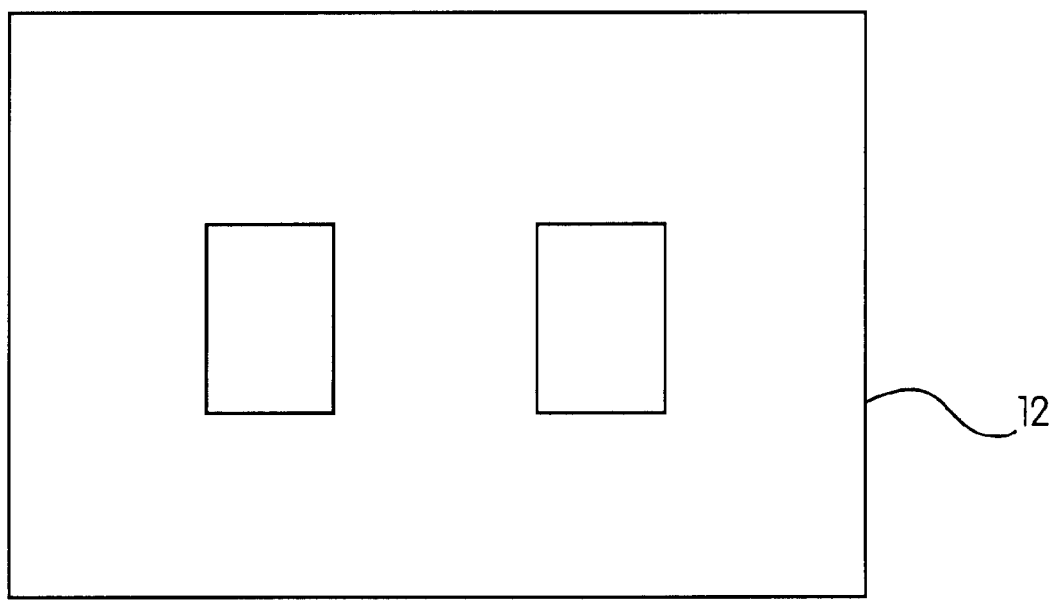
FIG. 2 is a perspective view of an embodiment of a heating pad with removable gel pack removed in accordance with the present invention.

Other features and advantages of the present invention will be apparent from the following description of the preferred embodiments thereof, and from the claims.

In order that the present invention may be readily understood, embodiments thereof will now be described, by way of example, with reference to the accompanying drawings.

DETAILED DESCRIPTION

In accordance with the exemplary embodiment illustrated in the drawings, the heating pad of the present invention includes a heating pad member 10 and a removable gel pack member 12. Heating pad member 10 is made up of a cover 13, padding 17 and electrical heating coils 18. The cover 13 comprises a first layer 14 and a second layer 15. The first layer 14 is an inner layer which contacts substantially the entire outer layer 21 of the gel pack member 12 and provides the interface through which thermal energy passes to the gel pack member 12, and the second layer 15 is an outer layer which provides the exterior surface of the heating pad. Each layer 14 and 15 comprises a flexible fabric material having a plurality of sides which are permanently secured together by means known in the art, for example, by stitching, riveting or stapling. Dispersed uniformly within the cover are padding 17 and the electrical heating coils 18 which are connectable to a suitable power source. The padding 17 consists of the typical filler materials used in heating pads, typically made from a nonflammable fiber or other flame-resistant or flame-retardant materials.

The removable gel pack member 12 is releasably attached to the second layer 14 of the heating pad cover 13, and comprises a heat-retentive gel which, in the practice of the subject invention, is heated to a predetermined temperature prior to attachment. In an exemplary embodiment of the present invention, the removable gel pack 12 contacts and covers substantially the entire inner layer 14 of the cover 13 of the heating pad member 10. The gel pack member 12 is typically constructed from two sheets (21 and 22) of a thin liquid-impermeable flexible plastic, such as vinyl or polyethylene. The outer layer 21 contacts substantially the entire inner layer 14 of the heating pad member 19, and provides the interface through which thermal energy flows from the removable gel pack 12 to the heating pad member 10. In an exemplary embodiment, the inner layer 22 of the removable gel pack 12 provides the interior surface of the heating pad. Thus, when the gel pack is placed in substantial contact with an anatomical portion of subject in need of heat therapy, heat is transferred to the subject through the interface formed by inner layer 22. The inner and outer sheets 22 and 21 are sealed along their edges by means known in the art, such as thermal welding or sealing, and as such form a leak-proof container for the gel. In addition, the gel pad member 12 may optionally have a temperature indicator 24, such as a tape containing an indicating temperature-sensitive liquid crystal substance, which would visually indicate to the user that the gel pack member 12 has been heated to an excessive temperature for normal use in a heating pad.

Figure 3A:
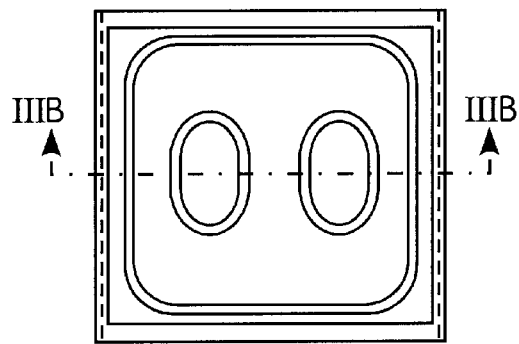
FIGS. 3A, 3B and 3C are top, side cross-sectional and top cross-sectional diagrammatic views of an embodiment of a heating pad with removable gel pack in accordance with the present invention.
Figure 3B:
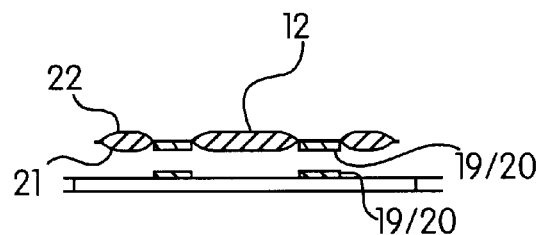
Figure 3C:
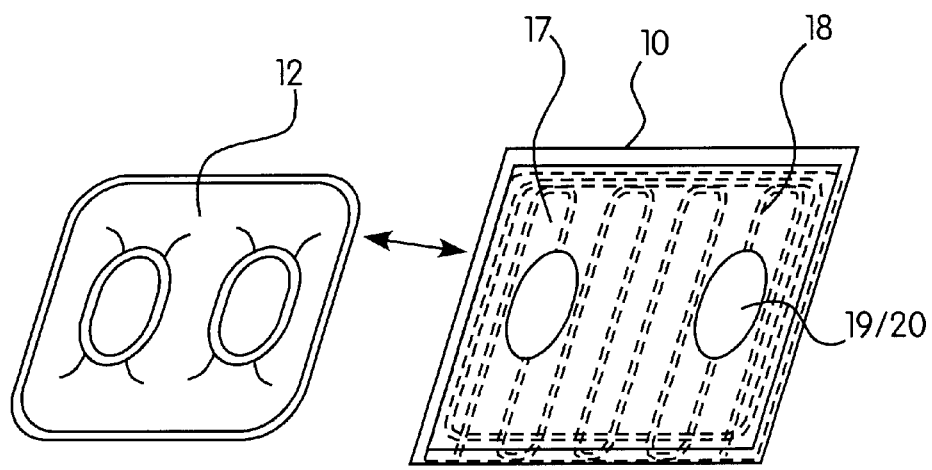
Figure 4:
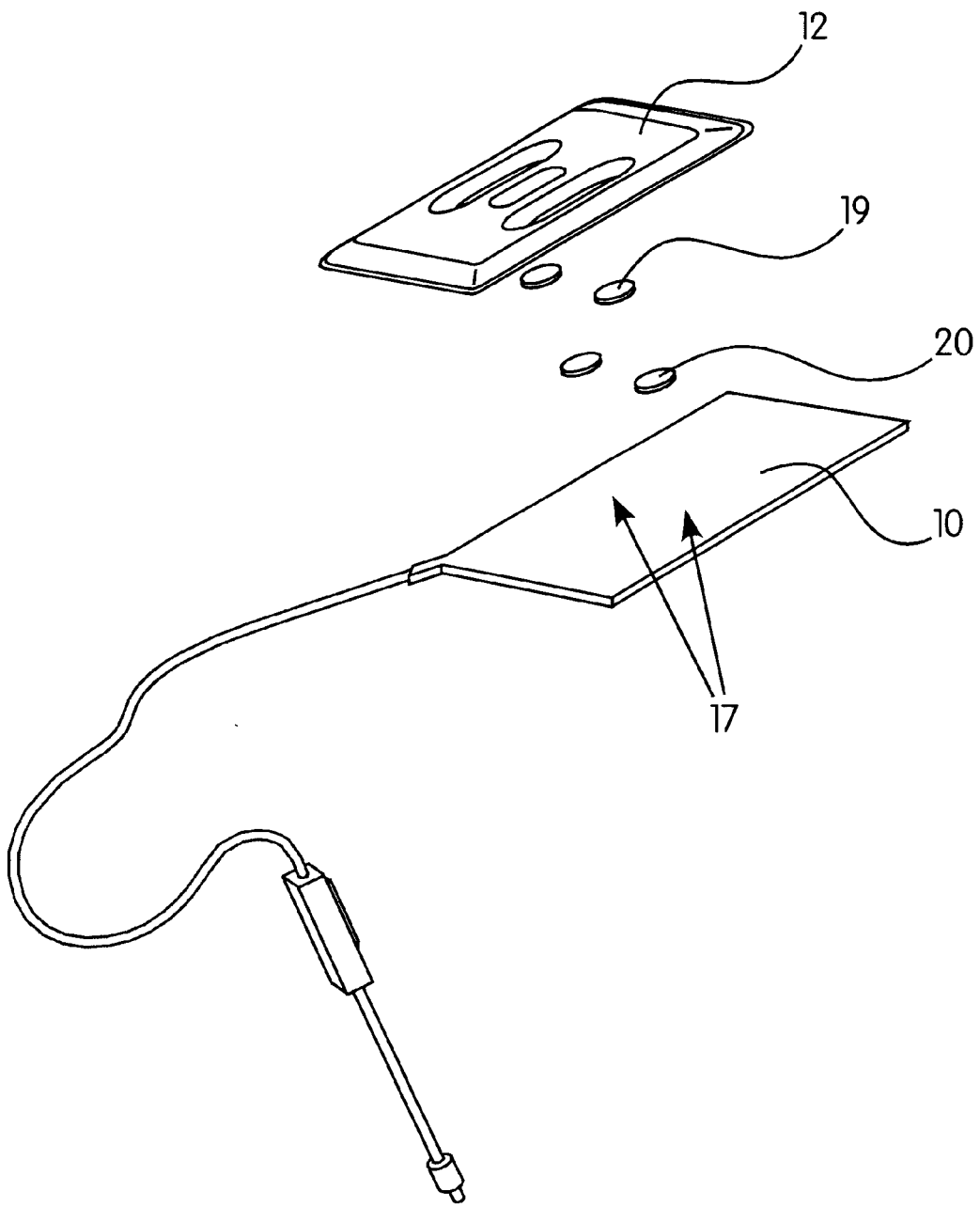
FIG. 4 is a side perspective diagrammatic exploded view of an embodiment of a heating pad with removable gel pack in accordance with the present invention.

In an exemplary embodiment of the present invention, the removable gel pack member 12 is attached to the heating pad member by two pairs of Velcro™-type hook and loop fasteners located respectively in complementary positions on the heating pad member and the removable gel pack (FIG. 3). Thus, the first layer 21 is modified by permanent attachment of at least one fastener 19 which may, for example, be of a hook or loop type, such as Velcro™, placed in position(s) so as to fasten to complementary fasteners 20 positioned on the inner layer 14 of the heating pad member 10 and thereby to stably attach the removable gel pack 12 to the heating pad member 10. The fasteners 19 and 20 are permanently attached by any method known in the art, such as by stitching, sewing, gluing, welding, riveting, etc.

In an alternative exemplary embodiment, an optional outer layer 21a and an optional inner layer 22a made from a plastic, nylon, vinyl or natural fiber fabric provide a protective cover for the gel pack member 12, wherein the outer and inner layers 21a and 22a are sealed along their peripheral edges by means known in the art, such as thermal welding or sealing, so as to form a pocket open on one side in which the gel pack member may be inserted during use. In this embodiment, heat is transferred to the subject through the interface formed by inner layer 22a. Accordingly, the outer layer 21a of the protective cover is modified by permanent attachment of at least one fastener 19 placed in position(s) so as to fasten to complementary fasteners 20 positioned on the inner layer 14 of the heating pad member 10. Such modification of outer layer 21a is useful in embodiments wherein a cutout is present corresponding substantially in location and dimension with each of the fasteners 19 and 20. In the latter embodiment, the gel pack 12 is maintained in stable position with respect to the heating pad member 10 by means of the releasably attached pocket formed by outer and inner layers 21a and 22a. As thus embodied, inner layer 22a provides the interior surface of the heating pad. The gel pack member 12 is maintained stably in the pocket during use by any means known in the art, including by friction between the gel pack member and the protective cover, a stabilizing fastener, clasp, hook/loop fasteners, etc., capable of releasably sealing the remaining open side, etc. In another embodiment, the ensemble of both the gel pack member 12 attached to the heating pad member 10 may be contained in a suitably shaped cover made from polyester, cotton, nylon or mixed fiber fabric. Such a cover may be releasably sealed by any means known in the art such as a clasp, loop/hook means or button.

Figure 5A:
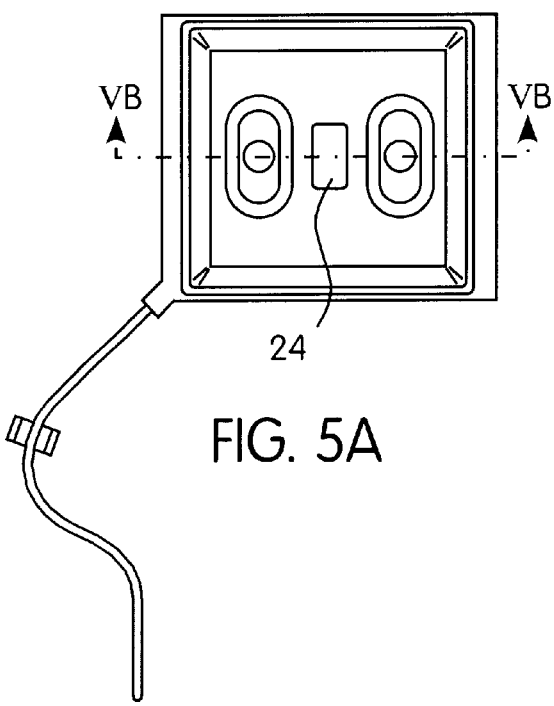
FIGS. 5A, 5B and 5C are top diagrammatic view and cross-sectional side diagrammatic views with detail of an embodiment of a heating pad with removable gel pack in accordance with the present invention.
Figure 5C:
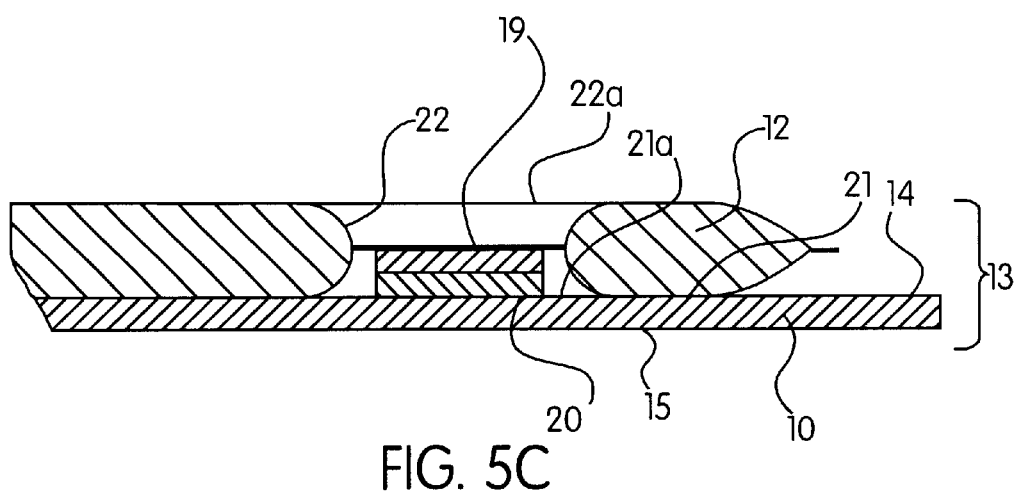
Figure 5B:
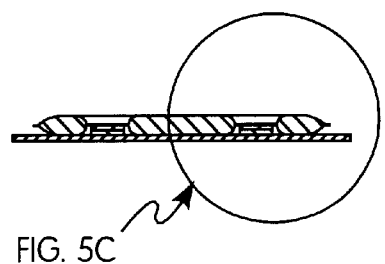
Figure 7A:
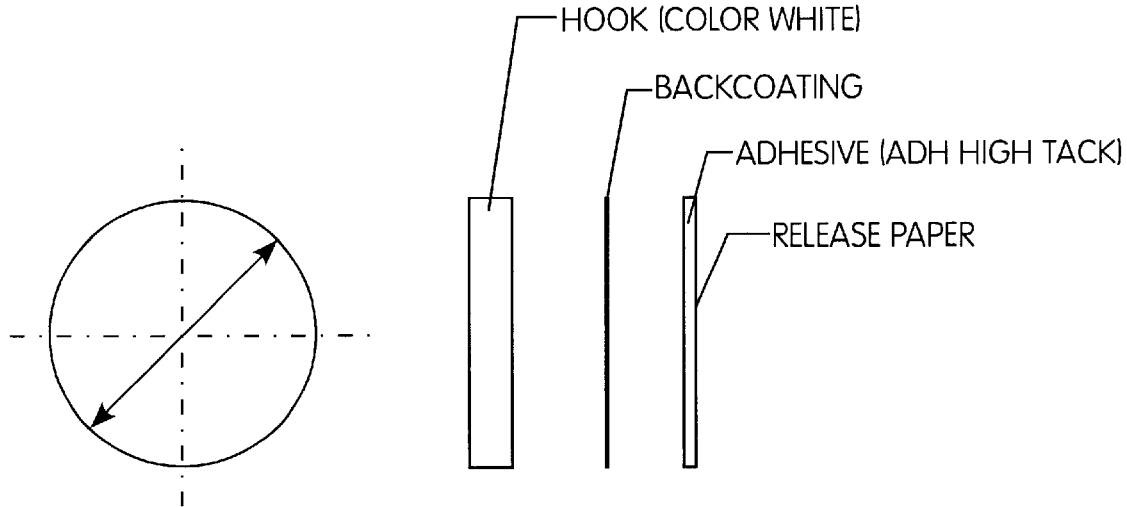
FIGS. 7A and 7B are top diagrammatic and cross-sectional exploded side diagrammatic views of Velcro™-type hook and loop patches in accordance with the present invention.
Figure 7B:
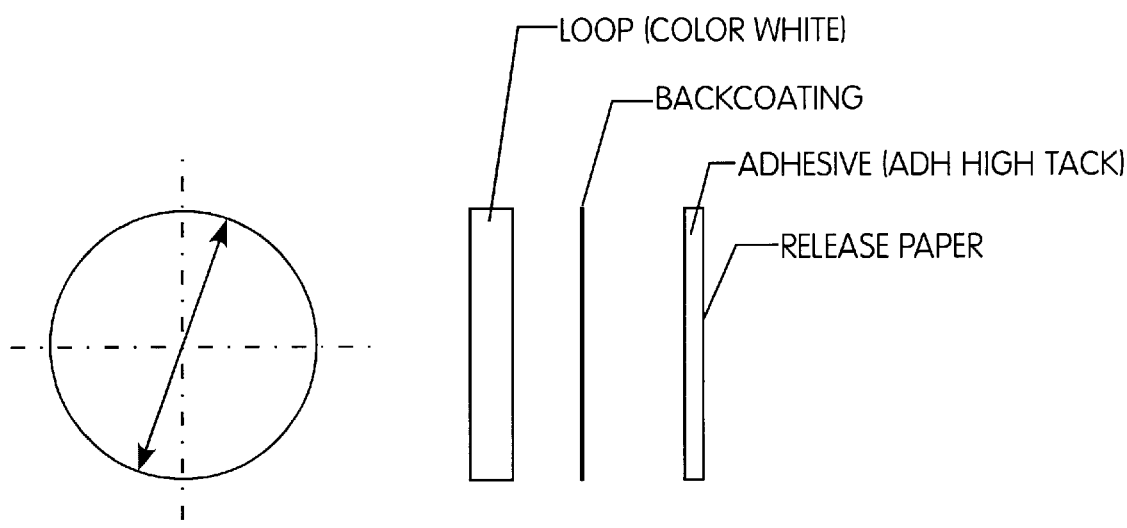

Referring to FIGS. 3, 5 and 6, the hook or loop fasteners 19 and 20 may be located at portions of the gel pack member 12 where the two layers 21 and 22 comprising the major sides of the gel pack are adjoined flush to one and other so as to form a unified plane 23 and to exclude the gel contents at the junction surface. These layers are adjoined by means known to those skilled in the art, including by means of thermal welding or epoxy gluing. The junction so formed should be capable of withstanding the typical thermal and mechanical stresses expected for the removable gel pack 12.

Referring to FIG. 3, the removable gel pack member 12 may be heated using any means consistent with the materials of which the gel pack is constructed. Most conveniently, the gel pack may be heated in a microwave oven to a predetermined temperature. Heating using a thermal heater such as under an infrared heater and in boiling water are alternative methods of heating the removable gel pack member 12 for use in the present invention.

In practice, the predetermined temperature is substantially maintained during application of the heating pad 10 to a portion of the anatomy of the subject after attachment of the gel pack 12 by passing a regulated current through the electrical heating coils 18. The electrical heating coils 18 are typically composed of metallic resistance wire or a conducting polymeric wire. The current useful for operating the electrical heating coils 18 may be of the alternating current type, such as 120V/60 Hertz household current, for operation in the home or workplace, or of the direct current type, such as 12V current, for convenient portable operation using a battery pack or in a vehicle, such as an automobile. After attachment of the removable gel pack 12 and the consequent rapid thermal transfer, the operating temperature can be maintained, raised or lowered for therapeutic relief or patient comfort by adjusting a suitable voltage controller (not shown) with or without automatic control mechanisms, including off-on proportional timers or thermostats.

One of skill in the art will readily understand that the present invention is not limited to the specific embodiments shown and described, and may be further used in applications other than therapeutic heating pads, such as heated bandages, stents, supports, etc.

Variations of the present invention may be made which are within the scope of the present invention as defined in the accompanying claims, without departing from the principles of the present invention.

Referring to FIGS. 3, 5 and 6, the hook or loop fasteners 19 and 20 may be located at portions of the gel pack member 12 where the two layers 21 and 22 comprising the major sides of the gel pack are adjoined flush to one and other so as to form a unified plane 23 and to exclude the gel contents at the junction interface. (FIG. SC) These layers are adjoined by means known to those skilled in the art, including by means of thermal welding or epoxy gluing. The junction so formed should be capable of withstanding the typical thermal and mechanical stresses expected for the removable gel pack 12.

Referring to FIG. 3, the removable gel pack member 12 may be heated using any means consistent with the materials of which the gel pack is constructed. Most conveniently, the gel pack may be heated in a microwave oven to a predetermined temperature. Heating using a thermal heater such as under an infrared heater is an alternative method of heating the removable gel pack member 12 for use in the present invention.

In practice, the predetermined temperature is substantially maintained during application of the heating pad 10 to a portion of the anatomy of the subject after attachment of the gel pack 12 by passing a regulated current through the electrical heating coils 18. The electrical heating coils 18 are typically composed of metallic resistance wire or a conducting polymeric wire. The current useful for operating the electrical heating coils 18 may be of the alternating current type, such as 120V/60 Hertz household current, for operation in the home or workplace, or of the direct current type, such as 12V current, for convenient portable operation using a battery pack or in a vehicle, such as an automobile. After attachment of the removable gel pack 12 and the consequent rapid thermal transfer, the operating temperature can be maintained, raised or lowered for therapeutic relief or patient comfort by adjusting a suitable voltage controller (not shown) with or without automatic control mechanisms, including off-on proportional timers or thermostats.

One of skill in the art will readily understand that the present invention is not limited to the specific embodiments shown and described, and may be further used in applications other than therapeutic heating pads, such as heated bandages, stents, supports, etc.

Variations of the present invention may be made which are within the scope of the present invention as defined in the accompanying claims, without departing from the principles of the present invention.

What is claimed is:

1. A heating pad comprising:
    a heating pad member comprising a cover and electrical heating coils, said cover comprising a first layer and a second layer, said first layer being an inner layer, and said second layer being an outer layer, each layer comprising a flexible fabric material and having a plurality of sides being permanently secured together, wherein the electrical heating coils are enclosed by the cover and substantially evenly distributed therewithin; and
    a removable gel pack member having an outer surface for contacting an anatomical portion of a subject, said removable gel pack member being releasably attached to said first layer of the cover of the heating pad member and comprising a heat-retentive gel which is heated to a predetermined temperature prior to attachment to the first layer of the cover of the heating pad member, wherein said pre-determined temperature is substantially maintained during application to the subject after said attachment by operating the electrical heating coils.

2. The heating pad in accord with claim 1, wherein the removable gel pack member is attached to the heating pad member by a plurality of fasteners located respectively in complementary positions on the heating pad member and the removable gel pack member.

3. The heating pad in accord with claim 2, wherein the fasteners are of the hook and loop type.

4. The heating pad in accord with claim 1, further comprising an automatic temperature control mechanism coupled to the electrical heating coils.

5. The heating pad in accord with claim 4, wherein the automatic temperature control mechanism includes an off-on proportional timer or a thermostat.

6. The heating pad in accord with claim 1, wherein the removable gel pack member can be heated in a thermal heater or in a microwave oven to the predetermined temperature.

7. The heating pad in accord with claim 6, wherein the predetermined temperature falls in a range between about 30 degrees Celsius and about 60 degrees Celsius.

8. The heating pad in accord with claim 1, wherein the first layer and the second layer of said cover of the heating pad member are secured together by stitching.

9. The heating pad in accord with claim 1, wherein the removable gel pack member further comprises two sheets of a thin liquid-impermeable flexible material selected from a group consisting of nylon, vinyl and polyethylene, said sheets forming a top sheet and a bottom sheet.

10. The heating pad in accord with claim 9, wherein the heating pad member contacts and covers substantially the entire bottom sheet of the removable gel pack member.

11. The heating pad in accord with claim 9, wherein the top sheet and bottom sheet of the removable gel pack member are sealed along their respective peripheral edges by thermal welding so as to form a liquid-impermeable junction.

12. The heating pad in accord with claim 9, wherein the removable gel pack member comprises a protective cover.

13. The heating pad in accord with claim 12, wherein the protective cover of the removable gel pack member comprises an inner layer and an outer layer, each layer comprising a nylon, plastic, vinyl or natural fiber fabric, said outer layer of the protective cover contacting the first layer of the heating pad member.

14. The heating pad in accord with claim 13, wherein the inner and outer layers of the protective cover for the removable gel pack member are sealed along their respective peripheral edges by thermal welding or sealing so as to form a pocket for the removable gel pack member.

15. The heating pad in accord with claim 12, wherein the removable gel pack member is releasably attached to the heating pad member by a plurality of fasteners located respectively in complementary positions on the first layer of the heating pad member and the outer layer of the protective cover of the removable gel pack member.

16. The heating pad in accord with claim 15, wherein the protective cover of the removable gel pack member further comprises cutouts on the outer layer of the protective cover of the removable gel pack member corresponding substantially in dimension and location to the fasteners such that the fasteners form a releasable attachment between the removable gel pack member and the heating pad member.

17. The heating pad in accord with claim 1, wherein the heating pad member is substantially planar.

18. The heating pad member in accord with claim 17, wherein the gel pack member is substantially planar.

19. A heating pad comprising:
    a substantially planar heating pad member comprising a cover and, electrical heating coils, said cover comprising a first layer and a second layer, said first layer being an inner layer, and said second layer being an outer layer, each layer comprising a flexible fabric material and having a plurality of sides being permanently secured together, wherein the electrical heating coils are enclosed by the cover and substantially evenly distributed therewithin; and
    a substantially planar removable gel pack member having an outer surface directly contacting an anatomical portion of a subject, said removable gel pack member being releasably attached to said first layer of the cover of the heating pad member and comprising a heat-retentive gel which is heated to a predetermined temperature prior to attachment to the first layer of the cover of the heating pad member, wherein said pre-determined temperature is substantially maintained during application to the subject after said attachment by operating the electrical heating coils.

20. The heating pad of claim 19, wherein the substantially planar removable gel pack is attached to the substantially planar heating pad member by a plurality of fasteners located respectively in complementary positions on the substantially planar heating pad member and the substantially planar removable gel pack member.

21. The heating pad of claim 20 wherein the fasteners are of the hook and loop type.

22. The heating pad of claim 19, further comprising an automatic temperature control mechanism connected to the electrical heating coils.

23. The heating pad of claim 22, wherein the automatic temperature control mechanism is an on-off proportional timer or a thermostat.

24. The heating pad of claim 19, wherein the substantially planar removable gel pack member can be heated in a thermal heater or in a microwave oven to the predetermined temperature.

25. The heating pad of claim 24, wherein the predetermined temperature falls in a range between about 30 degrees Celsius and about 60 degrees Celsius.

26. The heating pad of claim 19, herein the first layer and the second layer of said cover of the substantially planar heating pad member are secured together by stitching.

27. The heating pad of claim 19, wherein the substantially planar removable gel pack member further comprises two sheets of a thin liquid-impermeable flexible material selected from a group consisting of nylon, vinyl and polyethylene, said sheets forming a top sheet and a bottom sheet.

28. The heating pad of claim 27, wherein the top sheet and bottom sheet of the substantially planar removable gel pack member are sealed along their respective peripheral edges by thermal welding so as to form a liquid-impermeable junction.

29. The heating pad of claim 27, wherein the substantially planar removable gel pack member comprises a protective cover.

30. The heating pad of claim 29, wherein the protective cover of the substantially planar removable gel pack member comprises an inner layer and an outer layer, each layer comprising a nylon, plastic, vinyl or natural fiber fabric, said outer layer of the protective cover contacting the first layer of the substantially planar heating pad member.

31. The heating pad of claim 30, wherein the inner and outer layers of the protective cover for the substantially planar removable gel pack member are sealed along their respective peripheral edges by thermal welding or sealing so as to form a pocket for the substantially planar removable gel pack member.

32. The heating pad of claim 29, wherein the removable gel pack member is releasably attached to the heating pad member by a plurality of fasteners located respectively in complementary positions on the first layer of the heating pad member and the outer layer of the protective cover of the removable gel pack member.

33. The heating pad of claim 32, wherein the protective cover of the substantially planar removable gel pack member further comprises cutouts on the outer layer of the protective cover of the substantially planar removable gel pack member corresponding substantially in dimension and location to the fasteners such that the fasteners form a releasable attachment between the substantially planar removable gel pack member and the substantially planar heating pad member.

* * * * *